United States Patent [19]

Fujii et al.

[11] 4,224,342

[45] Sep. 23, 1980

[54] GUANIDINOBENZOIC ACID COMPOUNDS AND PROCESS FOR PREPARING THE SAME

[75] Inventors: Setsuro Fujii, Toyonaka; Tsuyoshi Watanabe, Kadoma; Masashi Shiota, Nishinomiya; Okumoto Itsuo, Ashiya; Naohiro Kayama, Takatsuki, all of Japan

[73] Assignee: Ono Pharmaceutical Co., Ltd., Osaka, Japan

[21] Appl. No.: 959,276

[22] Filed: Nov. 9, 1978

[30] Foreign Application Priority Data

Nov. 9, 1977 [JP] Japan ............................... 52-133379

[51] Int. Cl.$^2$ ................. A61K 31/155; A61K 31/245; C07C 129/12
[52] U.S. Cl. ................................... 424/310; 424/319; 560/34; 562/439
[58] Field of Search ................. 560/34; 424/310, 319; 562/439

[56] References Cited

U.S. PATENT DOCUMENTS 4,021,472  5/1977  Fujii et al. ............................... 560/34

FOREIGN PATENT DOCUMENTS 51-16631  2/1976  Japan ........................................ 560/34
49-11842  2/1974  Japan ........................................ 560/34

*Primary Examiner*—G. T. Breitenstein
*Attorney, Agent, or Firm*—Sughrue, Rothwell, Mion, Zinn and Macpeak

[57] ABSTRACT

Guanidinobenzoic acid compounds represented by the formula

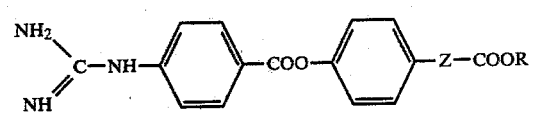

[I]

wherein R and Z are as defined hereinafter, having anti-plasmin and anti-trypsin activities and processes for preparing the same as well as a pharmaceutical composition and a method of inhibiting the activity of plasmin and a trypsin is disclosed.

10 Claims, No Drawings

GUANIDINOBENZOIC ACID COMPOUNDS AND PROCESS FOR PREPARING THE SAME

BACKGROUND OF THE INVENTION

1. Field of the Invention

This invention relates to novel guanidinobenzoic acid compounds and processes of producing the guanidinobenzoic acid compounds.

2. Description of the Prior Art

A number of compounds are known to have anti-plasmin and anti-trypsin activities. For example, trans-4-aminomethylcyclohexanecarboxylic acid as disclosed in S. Okamoto and U. Okamoto, *Keio Journal of Medicine*, 11, 105 (1962) is known to be an anti-plasmin agent. "Trasylol" as described in B. Kassel et al, *J. Biol. Chem.*, 238, 3274 (1963) and German Patent Application (OLS) No. 1,905,813 is known to be an anti-trypsin agent, and the compounds disclosed in U.S. Pat. No. 4,021,472 are known to be both an anti-plasmin agent and an anti-trypsin agent.

However, trans-4-aminomethylcyclohexanecarboxylic acid and Trasylol have disadvantages because they exhibit relatively low activities. The compounds described in U.S. Pat. No. 4,021,472 provide the same anti-plasmin or anti-trypsin effect at a lower dosage level than can be achieved with trans-4-aminomethylcyclohexanecarboxylic acid and Trasylol. However, there has been an increasing demand for compounds even more potent at a lower dosage level since reduced dosage generally means lowered side effects which is desirable from the standpoint of safety.

SUMMARY OF THE INVENTION

An object of this invention is, therefore, to provide guanidinobenzoic acid compounds which are useful as pharmaceuticals.

Another object of this invention is to provide guanidinobenzoic acid compounds of high potency with respect to anti-plasmin or anti-trypsin pharmacological activities at low dosage levels and to provide a process for preparing such compounds.

Another object of the present invention is to provide a pharmaceutical composition having antiplasmin and anti-trypsin activity:

A further object of the present invention is to provide a method for inhibiting the activity of plasmin and/or trypsin.

As a result of extensive research on anti-plasmin and anti-trypsin agents, it has now been found that a new series of guanidinobenzoic acid compounds have advantageous anti-plasmin and anti-trypsin activities.

Accordingly, this invention in one embodiment provides guanidinobenzoic acid compounds represented by the formula (I)

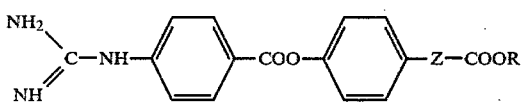

wherein Z represents a methylene group, an ethylene group or a vinylene group, and R represents a hydrogen atom or a lower alkyl group, the acid addition salts of the guanidinobenzoic acid compounds represented by the formula (I).

In another embodiment, this invention provides a process for preparing the guanidinobenzoic acid compounds represented by formula (I).

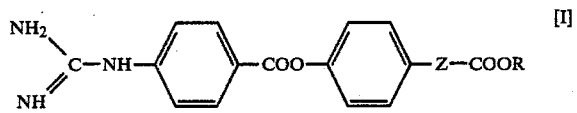

wherein Z represents a methylene group, an ethylene group or a vinylene group; and R represents a hydrogen atom or a lower alkyl group, and the acid addition salts thereof according to claim 1, comprising reacting a compound represented by the formula (II)

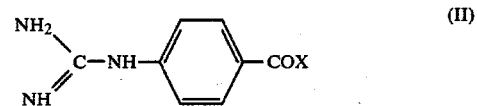

wherein X represents a halogen atom or an acid addition salt thereof with a compound represented by the formula (III)

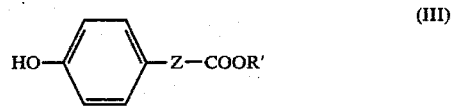

wherein Z has the same meaning as described above, and R' represents a hydrogen atom, a lower alkyl group or a protective group for a carboxylic acid group, and removing the protective group for a carboxylic acid group when R' represents a protective group for a carboxylic acid group.

DETAILED DESCRIPTION OF THE INVENTION

The term "lower alkyl" as is used throughout the specification and claims means a straight or branched chain alkyl group having 1 to 3 carbon atoms such as a methyl group, an ethyl group, n-propyl and isopropyl groups.

The novel guanidinobenzoic acid compounds can be prepared according to the following reaction scheme:

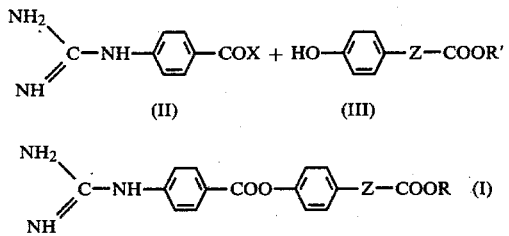

wherein Z and R are as defined above; X represents a halogen atom and R' represents a hydrogen atom, a lower alkyl group or a protective group for a carboxylic acid group.

The compounds of the formula (I) can be prepared by reacting a p-guanidinobenzoyl halide represented by the formula (II) or an acid addition salt thereof with a compound represented by the formula (III) in the presence of an inert solvent and a dehydrohalogenating agent at a temperature ranging from −20° C. to room temperature (about 10°–25° C.) for about 1 to 5 hours and then removing the protective group for a carboxylic acid group where R' represents such a protective group.

Suitable examples of dehydrohalogenating agents which can be used include tertiary amines such as triethylamine, tributylamine, N,N-dimethylaniline, N-methylpiperidine, pyridine, etc.

Suitable examples of inert solvents which can be used in this invention include benzene, toluene, diethyl ether, tetrahydrofuran, dioxane, acetone, acetonitrile, pyridine, etc.

The inert solvents described above can be used individually or as a mixture thereof. Of these inert solvents, pyridine is most preferred since it serves both as a solvent and as a dehydrohalogenating agent.

R' in the compounds represented by the formula (II) may be a hydrogen atom or a lower alkyl group, a protective group for a carboxylic acid group. It is, however, preferred to protect the carboxylic acid group.

Suitable examples of protective groups for carboxylic acid groups represented by R' which can be used in this invention include conventional protective groups for carboxylic acid groups such as a benzyl group, a t-butyl group, a trialkyl silyl group, e.g., a trimethylsilyl group, a p-methoxybenzyl group, etc., preferably a benzyl group and a t-butyl group with a benzyl group being most preferred.

The reaction product produced is in the form of an acid addition salt thereof. The acid addition salt reaction product may be isolated as it is by filtering the crystals precipitated in the reaction mixture or by adding an aqueous solution of sodium bicarbonate to the reaction mixture, thereby crystallizing the product in the form of a carbonate or an inner salt followed by filtration. When R' represents a hydrogen atom, the compound represented by the formula (I) is obtained as an inner salt and when R' represents a lower alkyl group or a protective group for a carboxylic acid group the compound is obtained as a carbonate salt.

Where the products are protected with a protective group for a carboxylic acid group, the protective group can be removed in a conventional manner.

For example, acid addition salts of the compound represented by the formula (I) can be obtained by removing the protective group for the carboxylic acid group by treating it with a mixed solution of hydrobromic acid and acetic acid when R' represents a benzyl group and with an acid such as hydrochloric acid, hydrobromic acid, sulfuric acid, trifluoroacetic acid, etc. when R' represents a t-butyl group, a p-methoxybenzyl group, etc.

The compound represented by the formula (I) can further be converted into pharmaceutically acceptable acid addition salts thereof with ease according to conventional methods, if desired.

Suitable examples of acids which can be used to produce the pharmaceutically acceptable acid additon salts include inorganic acids such as hydrochloric acid, sulfuric acid, phosphoric acid, hydrobromic acid, nitric acid, etc., and organic acids such as maleic acid, fumaric acid, malic acid, tartaric acid, citric acid, benzenesulfonic acid, toluenesulfonic acid, methanesulfonic acid, etc.

Preferred examples of pharmaceutically acceptable acid addition salts of the compound represented by the general formula (I) include methanesulfonates, toluene sulfonates, hydrochlorides, phosphates, etc.

The compounds of the formula (II) can be prepared from p-guanidinobenzoic acid in a conventional manner.

For example, p-guanidinobenzoic acid is heated with thionyl chloride to form p-guanidinobenzoyl chloride hydrochloride, which can be used per se for further reaction in this invention. (See German Pat. No. 950,637).

The compounds represented by the formula (III) are described in M. Tomita et al: *Tetrahedron Letters* 1967 1201, R. I. Meltzer et al: *J. Org. Chem.* 22, 1577 (1957), etc.

The compounds represented by the formula (I) and the acid addition salts thereof have potent anti-plasmin and anti-trypsin activities even at very low dosage levels.

The inhibitory activities of representative compounds of the formula (I) against plasmin and trypsin in vitro were determined in a manner similar to the method described by M. Muramatsu et al *J. Biochemistry* 58, 214 (1964) for trypsin and the method described by M. Muramatsu et al *J. Biochemistry* 57, 402 (1965) for plasmin. The procedures used are described more specifically below.

(1) Trypsin:

0.4 ml of trypsin (1.25 μg/m), 0.5 ml of p-tosylarginine methyl ester (20 mM) in Tris-HCl buffer (pH 8.5) and 0.1 ml of a solution of each of the following compounds represented by the formula (I) at various concentrations was reacted at a temperature of 37° C. for 30 minutes, and the concentration of each of the test compounds at which the activity of trypsin 0.5 μg to hydrolyze p-tosylargininmethyl ester was inhibited to an extent of 50% is shown in Table 1 below.

(2) Plasmin:

0.1 ml of human euglobulin (10 fold dilution), 0.1 ml of streptokinase (2000 unit/ml), 0.4 ml of fibrinogen (4% solution), 0.3 ml of a 0.1 M borate saline buffer solution (pH 7.4) and 0.1 ml of a solution of each of the following compounds represented by the formula (I) at various concentrations was allowed to react at a temperature of 37° C. for 30 minutes. The concentration at which the test compound exhibited inhibition against plasmin to an extent of 50% was determined, and the results obtained are shown in Table 1 below.

TABLE 1

| Test Compound | 50% Inhibition Concentration | |
|---|---|---|
| | Anti-Trypsin | Anti-Plasmin |
| P-(p-Guanidinobenzoyloxy)-phenylacetic Acid | $2.9 \times 10^{-8}$ M | $2.5 \times 10^{-7}$ M |
| Methyl p-(guanidino-benzoyloxy)phenylacetate | $9.0 \times 10^{-9}$ M | $2.2 \times 10^{-7}$ M |
| trans-4-Aminomethyl-cyclohexane Carboxylic Acid | | $3.0 \times 10^{-5}$ M |
| Trasylol | $2.8 \times 10^{-6}$ M | |

As is apparent from the above results, guanidinobenzoic acid compounds represented by the formula (I) and the acid addition salts thereof according to this invention are highly inhibitory to plasmin and trypsin and, therefore, are useful as pharmaceuticals, i.e., as an anti-trypsin agent for treating acute pancreatitis and the like or as an anti-plasmin agent for treating bleeding disorders and the like.

This invention also includes in its scope pharmaceutical compositions comprising at least one of the compounds represented by the general formula [I] or pharmaceutically acceptable salts thereof and pharmaceutically acceptable carriers, diluents and excipients.

Usually the compounds or pharmaceutical compositions comprising the same are administered orally. Suitable examples of solid formulations for oral administration include tablets, pills, powders and granules. In these solid formulations one or more active ingredients are mixed with at least one inactive diluent such as calcium carbonate, potato starch, alginic acid, lactose, etc. The formulation may contain additives other than the diluents, for example, lubricants such as magnesium stearate, etc.

Suitable example of liquid formulations for oral administration include pharmaceutically acceptable emulsions, solutions, suspensions, syrups or elixirs. Conventionally used liquid diluents are, for example, water or liquid paraffin. This formulation may also contain, in addition to the diluents, auxiliary agents, for example, humectants, suspension aids, sweeteners, flavors, fragrants or antiseptics.

Capsules comprising an assimilable substance such as gelatin and which contain one or more active ingredients and a diluent or an excipient can also be used in this invention as a suitable example of formulation for oral administration.

In this invention the amount of the active ingredient in the formulation can be varied and a suitable amount determined depending on the therapeutic purpose. Dosage is determined based on the therapeutic effects desired, the number of times administered and the period of treating.

Usually, the dosage for an adult is about 100 mg to about 1 g per patient per day for treating acute pancreatitis and hemorrhagic diseases by oral administration.

Acute toxicity of 4-(4-guanidinobenzoyloxy)phenylacetic acid mesylate, one of the compounds of this invention represented by the general formula (I) is 4500 mg/kg in mice and 4400 mg/kg in rats.

Preferred specific examples of guanidinobenzoic acid compounds represented by formula (I) of this invention include p-(guanidinobenzoyloxy)phenylacetic acid, 3-[p-(p-guanidinobenzoyloxy)penyl]propionic acid, p-(p-guanidinobenzoyloxy)cinnamic acid, methyl p-(p-guanidinobenzoyloxy)phenyl acetate, ethyl p-(p-guanidinobenzoyloxy)phenyl acetate, n-propyl p-(p-guanidinobenzoyloxy)phenyl acetate, isopropyl p-(p-guanidinobenzoyloxy)phenyl acetate, methyl p-(p-guanidinobenzoyloxy)phenyl propionate, ethyl p-(p-guanidinobenzoyloxy)phenylpropionate, methyl p-(p-guanidinobenzoyloxy)cinnamate, etc.

This invention is illustrated in further detail by reference to the following Examples, but it should be understood that they are given for illustrative purposes only and are not to be construed as limiting the scope of the invention. Unless otherwise indicated, all parts, percents, ratios and the like are by weight and all operations below were conducted at atmospheric pressure.

EXAMPLE 1

P-(p-Guanidinobenzoyloxy)phenylacetic Acid and Methanesulfonate Thereof 17 g of p-guanidinobenzoic acid was heated with 70 ml of thionyl chloride for 30 minutes with stirring. To the resulting mixture was added petroleum ether to precipitate crystals, which were filtered and washed with petroleum ether.

The crystals thus obtained were added to 250 ml of pyridine, having 23 g of benzyl p-hydroxyphenylacetate dissolved therein at $-20°$ C. and the mixture was stirred at $0°$ C. for 5 hours. The reaction mixture was filtered and the filtrate was concentrated to about half the original volume followed by adding diethyl ether thereto. The oily product obtained was removed by decantation and water was added thereto. The resulting crystals were filtered out, washed twice with water and recrystallized once from a mixture of acetone-diethyl ether (v/V ratio: 2:1) to obtain 21.5 g of benzyl p-(p-guanidinobenzoyloxy)phenylacetate hydrochloride having a melting point 123° to 127° C. 17.5 g of this compound was added to 125 g of a 28% hydrobromic acid acetic acid solution. After allowing the mixture to stand at room temperature for 2 hours, 800 ml of diethyl ether was added thereto. The resulting crystals were washed with diethyl ether and dried. The dried crystals were dissolved in a mixed solvent of water-methanol (v/V ratio: 1:1) followed by adding saturated aqueous solution of sodium bicarbonate to precipitate crystals of p-(p-guanidinobenzoyloxy)phenylacetic acid having a melting point of 242° to 246° C.

9 g of the crystals thus obtained were suspended in methanol and the resulting suspension was made acidic (pH 3) with methanesulfonic acid and diethyl ether was added thereto to precipitate crystals, which were then filtered out. Recrystallization thereof from methanol afforded 8.1 g of p-(p-guanidinobenzoyloxy)phenylacetic acid methanesulfonate having a melting point of 203° to 205° C.

Elemental Analysis for $C_{16}H_{15}N_3)_4 \cdot CH_3SO_3H$. Calculated (%): C 49.87; H 4.68; N 10.27; S 7.83. Found (%): C 49.69; H 4.51; N 10.34; S 7.65.

EXAMPLE 2

Methyl p-(p-Guanidinobenzoyloxy)phenyl Acetate Mesylate 3.60 g of p-guanidinobenzoic acid was converted into p-guanidinobenzoyl chloride hydrochloride in the same manner as described in Example 1. This compound was added to 27 ml of pyridine, having 3.36 g of methyl p-hydroxyphenylacetate dissolved therein, at 0° C. and the mixture was stirred at 0° C. for 2 hours. To the reaction mixture was added saturated sodium bicarbonate aqueous solution to precipitate crystals, which were then filtered, washed with water and acetone, and then dried. The dried crystals were suspended in methanol and the suspension was made weakly acidic (pH 3) with methanesulfonic acid. Then, diethyl ether was added thereto to precipitate crystals. Recrystallization thereof from methanol afforded 2.83 g of methyl p-(p-guanidinobenzoyloxy)phenylacetate mesylate having a melting point of 146°-148° C.

Elemental Analysis for $C_{17}H_{17}N_3O_4 \cdot CH_3SO_3H$. Calculated (%): C 51.05; H 5.00; N 9.93; S 7.57. Found (%): C 51.26; H 5.18; N 9.84; S 7.41.

While the invention has been described in detail and with reference to specific embodiments thereof, it will be apparent to one skilled in the art that various changes and modifications can be made therein without departing from the spirit and scope thereof.

What is claimed is:

1. A guanidinobenzoic acid compound represented by the formula (I)

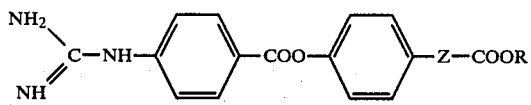

wherein Z represents a methylene group, an ethylene group or a vinylene group; and R represents a hydrogen atom or a lower alkyl group, and the acid addition salts thereof.

2. The guanidinobenzoic acid compound according to claim 1, wherein said acid addition salts are salts of an acid selected from the group consisting of hydrochloric acid, sulfuric acid, phosphoric acid, hydrobromic acid, nitric acid, acetic acid, lactic acid, oxalic acid, maleic acid, fumaric acid, malic acid, tartaric acid, citric acid, benzenesulfonic acid, toluenesulfonic acid and methanesulfonic acid.

3. p(p-Guanidinobenzoyloxy)phenylacetic acid and the acid addition salts thereof, according to claim 2.

4. 3-[p-(p-Guanidinobenzoyloxy)phenyl]propionic acid and the acid addition salts thereof, according to claim 2.

5. p-(p-Guanidinobenzoyloxy)cinnamic acid and the acid addition salts thereof, according to claim 2.

6. Methyl p-(p-guanidinobenzoyloxy)phenylacetate and the acid addition salts thereof, according to claim 2.

7. Methyl 3-[p-(p-Guanidinobenzoyloxy)phenyl]propionate and the acid addition salts thereof, according to claim 2.

8. Methyl p-(p-Guanidinobenzoyloxy)cinnamate and the acid addition salts thereof, according to claim 2.

9. A pharmaceutical composition having antiplasmin and anti-trypsin activity comprising a therpeautically effective amount of at least one guanidinobenzoic acid compound represented by the formula (I) and the acid addition salts thereof according to claim 1, and one or more pharmaceutically acceptable carriers or diluents.

10. A method of inhibiting the activity of plasmin and/or trypsin comprising administering a therpeautically effective amount of at least one guanidinobenzoic acid compound represented by the formula (I) or the acid addition salts thereof according to claim 1 to a subject.

* * * * *